United States Patent [19]
Willis

[11] Patent Number: 5,233,308
[45] Date of Patent: Aug. 3, 1993

[54] THERMAL CONDUCTIVITY CELL

[75] Inventor: Peter M. Willis, Benton Harbor, Mich.

[73] Assignee: Leco Corporation, Benton Harbor, Mich.

[21] Appl. No.: 847,797

[22] Filed: Mar. 6, 1992

[51] Int. Cl.⁵ .......................................... G01N 25/18
[52] U.S. Cl. .................... 324/706; 324/450; 204/406; 73/25.03
[58] Field of Search ............ 324/706, 439, 425, 450; 204/406; 73/25.03, 23.40, 23.25

[56] References Cited

U.S. PATENT DOCUMENTS

| | | | |
|---|---|---|---|
| 2,926,520 | 3/1960 | Schmauch | 73/25.03 |
| 3,512,080 | 5/1970 | Hanson | 324/450 |
| 3,683,671 | 8/1972 | Van Swaay | 324/706 |
| 4,164,862 | 8/1979 | Jackson | 73/25.03 |
| 4,384,934 | 5/1983 | de Bruin et al. | 324/706 |
| 4,461,166 | 7/1984 | Gatten et al. | 73/25.03 |
| 4,594,879 | 6/1986 | Maeda et al. | 73/25.03 |
| 4,741,198 | 5/1988 | Farren et al. | 73/23.4 |
| 4,918,974 | 4/1990 | Hachey et al. | 73/25.03 |

Primary Examiner—Kenneth A. Wieder
Assistant Examiner—Maura Regan
Attorney, Agent, or Firm—Price, Heneveld, Cooper, DeWitt & Litton

[57] ABSTRACT

A thermal conductivity cell in the form of a bridge is used as one of the resistors in a Wheatstone bridge network. The output of the thermal conductivity cell is applied to the input of a low noise amplifier, the output of which is differentiated by an R-C coupling network having a time constant selected to pass a substantial portion of the output signal from the thermal conductivity cell with minimum attentuation. The R-C differentiating coupling network effectively reduces DC errors due to drift and offset and shapes the output signal improving the signal-to-noise ratio enabling trace amounts of materials to be analyzed.

4 Claims, 2 Drawing Sheets

THERMAL CONDUCTIVITY CELL

BACKGROUND OF THE INVENTION

Thermal conductivity cells are commonly used in the quantitative analysis of chemical constituents. A conductivity cell consists of a bridge network made up of thin resistive wires. The change in resistance of the bridge caused by the thermal conductivity of the material being measured provides an output signal which can be used to measure the amount of the material present in the gas stream flowing through the conductivity cell.

Great care must be exercised in the use and handling of a thermal conductivity cell to protect the thin filament wires. The cell is normally heated to a constant temperature for the thermal conductivity measurement. The heat is generated by passing current through the filament wires. It normally takes several hours before the resistors making up the bridge network in the thermal conductivity cell settle down or stabilize before the cell can be used. Also, when adjustments are made to the cell, such as the familiar offset adjustment, it takes several hours before the effect of the adjustment can be observed and several more hours if additional adjustments have to be made.

Also, it is important to minimize the effect of common mode or drift errors in the bridge and to reduce the effects of noise on the data signal representative of the amount of a constituent material in the sample being analyzed.

SUMMARY OF THE INVENTION

The improved thermal conductivity cell includes a resistive bridge network which includes the thermal conductivity filaments in one leg of the resistive bridge network. A current source is provided for heating the thermal conductivity cell. A linearization circuit is provided which causes the changes in voltage across the bridge to be a linear function of the change in resistance of the bridge. The output of the thermal conductivity cell is coupled through a low noise amplifier and an R-C coupling network to provide an output signal substantially free from errors due to noise, drift and offset variables. The R-C coupling circuit also speeds up the initial adjustment of the thermal conductivity cell.

DETAILED DESCRIPTION OF THE PREFERRED EMBODIMENTS

Figure 1:
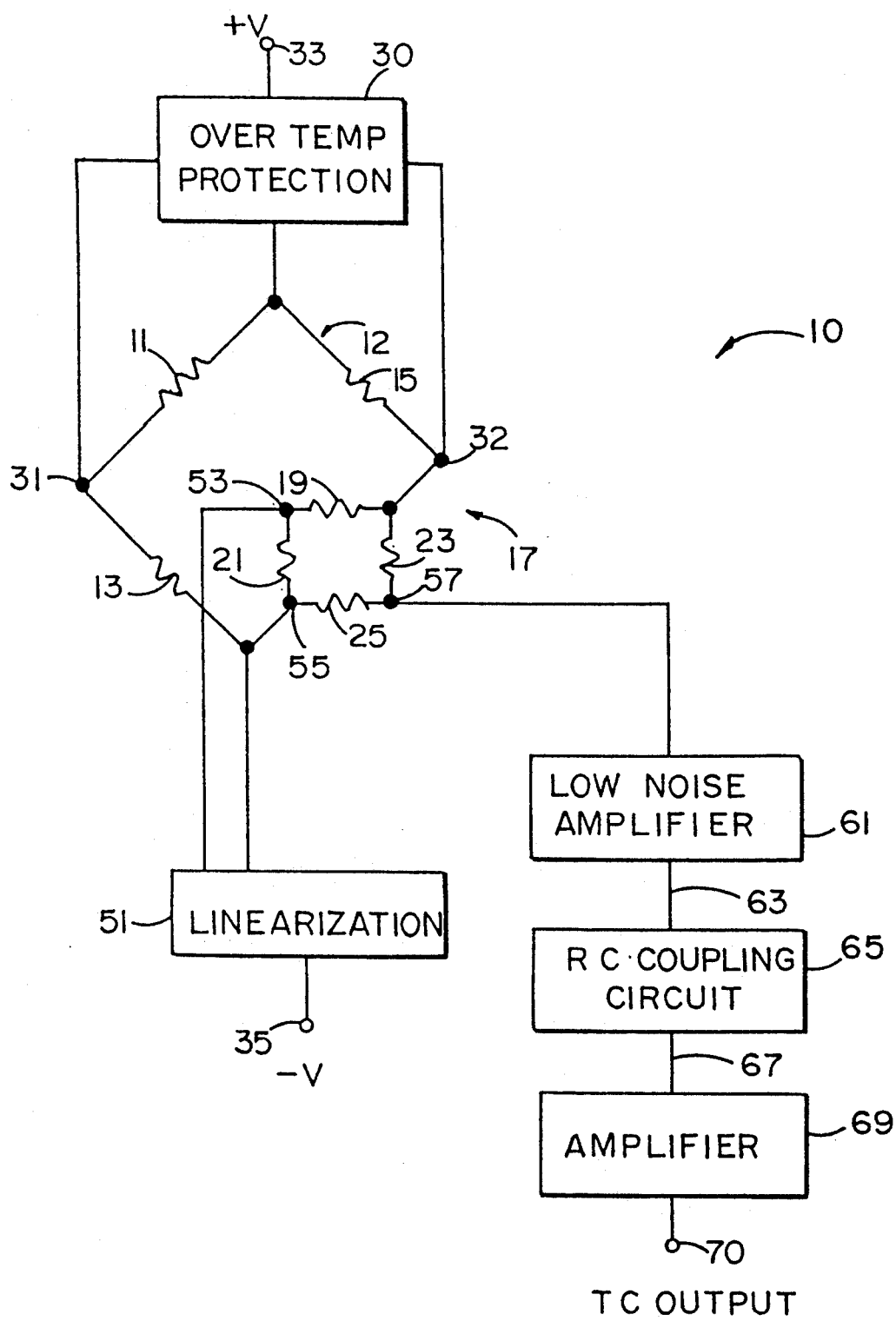
FIG. 1 is a block diagram of a preferred embodiment of the linearization and output circuits according to the invention.

Referring now to FIG. 1, the circuit includes a first bridge network made up of resistors 11, 13 and 15 and a second bridge network 17 forming the fourth leg of the first bridge network. The second bridge network is the thermal conductivity cell and is made up of thin resistive filaments 19, 21, 23 and 25. An over-temperature protection circuit indicated by the number 30 is connected to nodes 31 and 32 of the first bridge network. The over-temperature circuit protects the thin filament wires in the thermal conductivity cell from destructive over heating. The resistive bridge networks are connected between a positive potential source 33 and a negative potential source 35.

A linearization circuit 51 is provided across nodes 53 and 55 of the thermal conductivity cell. Linearization circuit 51 essentially pulls node 53 to ground potential causing output node 57 across the bridge from node 53 to passively follow and approach ground potential. Having the opposed nodes of the bridge at essentially ground potential substantially eliminates common mode errors caused by changes in resistance value in the resistors in each arm of thermal conductivity cell 17.

The output of the thermal conductivity cell is taken from node 57 through a low noise amplifier 61. The output of the amplifier is connected by line 63 to an R-C coupling circuit 65 which functions as a differentiator for the output signal from the low noise amplifier 61, passing the output signal from the thermal conductivity cell and substantially eliminating drift and offset problems. The coupling network feeds the signal on line 67 to an amplifier 69 which amplifies the desired signal sending the signal to an output 70. Through the use of low noise amplifier 61 and coupling circuit 65, the signal to noise ratio is substantially improved.

Figure 2:
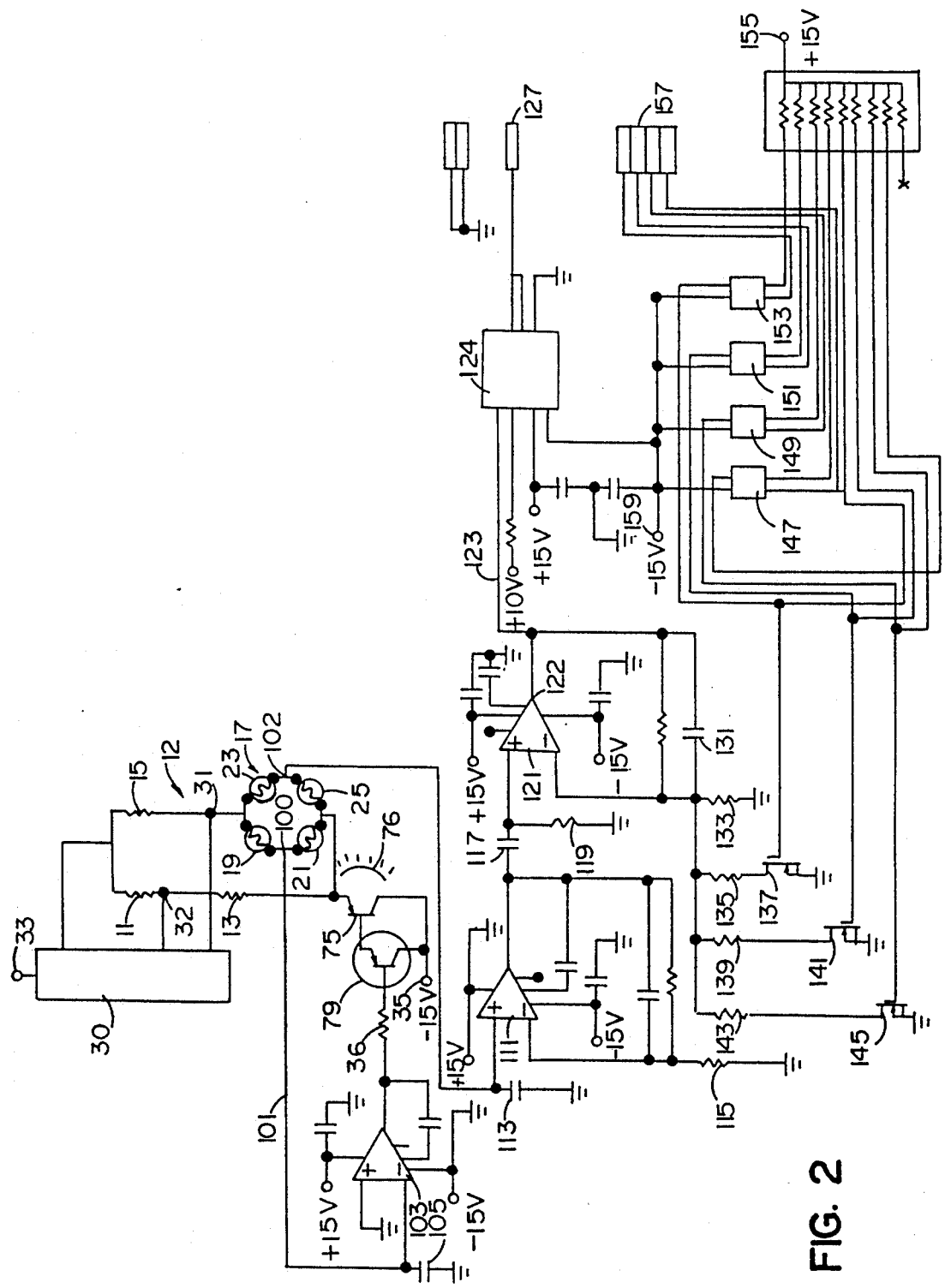
FIG. 2 is a schematic diagram of the circuits of FIG. 1.

Turning now to FIG. 2, a schematic diagram of a preferred embodiment of the electronics used to implement the present invention is shown.

One corner of the bridge in thermal conductivity cell 17 is connected by line 101 to the inverting input of low noise operational amplifier 103. Noise and other high frequency signals on line 101 are by-passed to ground through capacitor 105. The non-inverting input of operational amplifier 103 is connected to ground which, in turn, tends to cause node 100 of the thermal conductivity cell to be drawn toward ground. In view of the nature of a Wheatstone bridge, if node 100 is pulled toward ground, node 102 will passively follow and also approach ground potential. The linearization circuit causes the changes in voltage across the bridge to be a linear function of the change in resistance of the bridge.

The output of operational amplifier 103 is applied through resistor 36 to the base of PNP transistor 79 and determines the current flow through transistor 79 and PNP transistor 75. The over-temperature protection circuit 30, along with PNP transistors 75 and 79 determine the overall current flow through bridge networks 12 and 17. If the electronics are implemented on a printed circuit board, which is preferred, the traces for the current path through these transistors should be heavy enough to carry the current without excessive voltage drop.

The output signal from the thermal conductivity cell is taken from node 102 and is applied to the non-inverting input of operational amplifier 111. Capacitor 113 is coupled to node 102 and to ground and by-passes high frequency noise. The inverting input of operational amplifier 111 is connected to ground through resistor 115. Nodes 100 and 102 of the thermal conductivity cell both exhibit a resistance of approximately 50 ohms. Operational amplifiers 103 and 111 are selected to match this impedance and to be very low noise devices. The preferred low noise operational amplifier can be obtained from Linear Technology of Milpitas, California and are identified by Part No. LT-1028. Operational amplifier 111 has a gain of approximately 50 and raises the signal above the noise floor, the noise primarily being developed in resistor 119 which is connected to the output of the amplifier.

The output of operational amplifier 111 is coupled to capacitor 117 which, in turn, is coupled to resistor R119 which is connected from one side of capacitor 117 to ground. The R-C coupling network functions as a differentiator for the output signal. The time constant for the R-C network should be selected to pass a substantial portion of the desired output signal with minimum attenuation. In the preferred embodiment, C117 is approximately 5 microfarads and R119 is approximately 649K ohms. The capacitor C117 effectively blocks any DC sources of error, such as offset and drift, and passes the AC component of the output signal from the thermal conductivity cell to the non-inverting input of operational amplifier 121 which functions as a conventional amplifier for the output signal. The output of operational amplifier 121 is coupled by a line 123 to a voltage level shifter 124 and then to output 127. The output voltage is level shifted so that the desired signal from the thermal conductivity cell is centered about +4 volts.

The output 122 of operational amplifier 121 is connected through a capacitor 131 to a variable gain circuit. Capacitor 131 is connected to a resistor 133 which is connected directly to ground. The capacitor is also connected to a resistor 135 which is connected through an MOS device 137 to ground. The output is also connected to resistor 139 which is coupled to ground through MOS device 141 and again the output is connected to resistor 143 which is connected to ground through MOS device 145.

Optical coupling devices 147, 149, 151 and 153 are connected between a positive source of voltage 155 and a selection circuit 157 by means of which the light emitting diode in each optical coupler can be illuminated, turning the device hard on and bringing the gates of the selected MOS devices 137, 141 and 145 to a source of negative potential 159 which causes the selected MOS device to be turned off disconnecting the resistor in series with the device to ground. Various combinations of the resistor/MOS device circuits can be selected to provide eight levels of gain for amplifier 121.

The output circuit for the thermal conductivity cell provides a very low noise output signal substantially free of DC errors, such as common mode and offset problems.

By means of the present invention, the change in voltage across the thermal conductivity cell will be a linear function of the change in resistance of the cell. Also, the output of the thermal conductivity cell is amplified through an extremely low noise amplifier and is then R-C coupled to a second amplifier stage before the output. The R-C coupling network effectively reduces DC errors due to drift and offset problems and since the coupling network functions as a differentiating circuit, a sharper output signal is obtained from the thermal conductivity cell. The improved output enables trace amounts of materials to be effectively analyzed by means of the thermal conductivity cell.

Since drift and offset are essentially DC problems, the R-C coupling network tends to minimize the effect of the variables on the output signal. Changes can then be made in the operation of the thermal conductivity cell and the affect of the change can be seen more quickly in the output of the cell without waiting the usual period of time for the cell to stabilize.

Although the invention has been described with respect to specific preferred embodiments thereof, many variations and modifications will become apparent to those skilled in the art. It is, therefore, the intention that the appended claims be interpreted as broadly as possible in view of the prior art to include all such variations and modifications.

The embodiments of the invention in which an exclusive property or privilege is claimed are defined as follows:

1. An improved thermal conductivity cell comprising:
    a thermal conductivity cell in the form of a resistive bridge network;
    a first resistive bridge network including said thermal conductivity cell in one leg of said first resistive bridge network;
    a current source for heating said thermal conductivity cell;
    a low noise amplifier coupled to said thermal conductivity cell for amplifying the signal produced by said thermal conductivity cell in measuring the thermal conductivity of a material;
    an R-C coupling network connected to the output of said low noise amplifier for filtering out undesirable noise and for passing the amplified detected signal related to the thermal conductivity of a material.

2. An improved thermal conductivity cell as set forth in claim 1, wherein said low noise amplifier is a low noise operational amplifier having an input resistance substantially equal to the output node resistance of the thermal conductivity cell.

3. An improved thermal conductivity cell as set forth in claim 1, wherein said coupling network is a differentiating network having a time constant selected to pass a substantial portion of the output signal with low attenuation.

4. An improved thermal conductivity cell as set forth in claim 3, wherein said differentiating network is an R-C network having a time constant selected to pass the amplified measurement signal from said thermal conductivity cell.

* * * * *

UNITED STATES PATENT AND TRADEMARK OFFICE
CERTIFICATE OF CORRECTION

PATENT NO. : 5,233,308
DATED : August 3, 1993
INVENTOR(S) : Peter M. Willis

It is certified that error appears in the above-indentified patent and that said Letters Patent is hereby corrected as shown below:

Column 1, line 51: after "the" insert --present--

Signed and Sealed this

Sixth Day of September, 1994

Attest:

BRUCE LEHMAN

Attesting Officer — Commissioner of Patents and Trademarks